United States Patent
Bricker et al.

(10) Patent No.: US 6,673,979 B1
(45) Date of Patent: *Jan. 6, 2004

(54) PROCESS FOR SEPARATING ALKYLAROMATIC HYDROCARBONS

(75) Inventors: Maureen L. Bricker, Buffalo Grove, IL (US); Charles P. McGonegal, Addison, IL (US); Herman A. Zinnen, Evanston, IL (US)

(73) Assignee: UOP LLC, Des Plaines, IL (US)

(*) Notice: Subject to any disclaimer, the term of this patent is extended or adjusted under 35 U.S.C. 154(b) by 103 days.

This patent is subject to a terminal disclaimer.

(21) Appl. No.: 10/086,485

(22) Filed: Mar. 1, 2002

Related U.S. Application Data

(63) Continuation-in-part of application No. 09/850,632, filed on May 7, 2001, now Pat. No. 6,403,856, which is a continuation-in-part of application No. 09/430,893, filed on Nov. 1, 1999, now Pat. No. 6,274,784, which is a continuation-in-part of application No. 09/175,116, filed on Oct. 19, 1998, now Pat. No. 6,005,153.

(51) Int. Cl.$^7$ .................................................. C07C 7/13
(52) U.S. Cl. ........................................ 585/828; 585/831
(58) Field of Search ............................... 585/828, 831

(56) References Cited

U.S. PATENT DOCUMENTS

| | | | |
|---|---|---|---|
| 2,836,633 A | 5/1958 | Esmay et al. | 260/671 |
| 3,122,494 A | 2/1964 | Brown et al. | 208/63 |
| 3,211,798 A | 10/1965 | Burk, Jr. et al. | 260/668 |
| 3,943,183 A | 3/1976 | Rosback | 260/674 SA |
| 3,997,620 A | 12/1976 | Neuzil | 260/674 SA |
| 3,998,901 A | 12/1976 | Neuzil et al. | 260/674 SA |
| 4,028,428 A | 6/1977 | Neuzil et al. | 260/674 SA |
| 4,051,192 A | 9/1977 | Neuzil et al. | 260/674 SA |
| 4,079,094 A | 3/1978 | Rosback et al. | 260/674 SA |
| 4,255,607 A | 3/1981 | Miyake et al. | 585/805 |
| 4,956,522 A | 9/1990 | Zinnen | 585/828 |
| 5,012,038 A | 4/1991 | Zinnen | 585/828 |
| 5,530,172 A | 6/1996 | Funk et al. | 585/736 |
| 5,530,173 A | 6/1996 | Funk et al. | 585/737 |
| 5,744,683 A | 4/1998 | Dandekar et al. | 585/736 |
| 5,744,684 A | 4/1998 | Zinnen et al. | 585/737 |
| 5,877,373 A | 3/1999 | Zinnen et al. | 585/475 |
| 6,008,424 A | 12/1999 | Zinnen et al. | 585/475 |

*Primary Examiner*—Thuan D. Dang
(74) *Attorney, Agent, or Firm*—John G. Tolomei; Frank S. Molinaro; Maryann Maas

(57) ABSTRACT

A process for separating at least one $C_8$ alkylaromatic hydrocarbon from a mixture containing at least one $C_8$ alkylaromatic hydrocarbon and at least one $C_9$ or $C_{10}$ alkylaromatic hydrocarbon using dealuminated sodium zeolite Y.

5 Claims, 4 Drawing Sheets

PROCESS FOR SEPARATING ALKYLAROMATIC HYDROCARBONS

CROSS REFERENCE TO RELATED APPLICATION

This application is a continuation-in-part of our application Ser. No. 09/850,632, filed May 7, 2001, now U.S. Pat. No. 6,403,856 hereby incorporated by reference in its entirety, which in turn is a continuation-in-part of application Ser. No. 09/430,893 filed Nov. 1, 1999, now U.S. Pat. No. 6,274,784 B1, hereby incorporated by reference in its entirety, which in turn is a continuation-in-part of application Ser. No. 09/175,116, filed Oct. 19, 1998, now U.S. Pat. No. 6,005,153 B1 all of which is hereby incorporated by reference.

FIELD OF THE INVENTION

The invention is a process for separating $C_8$ alkylaromatic hydrocarbons from $C_9$ and $C_{10}$ alkylaromatic hydrocarbons.

BACKGROUND OF THE INVENTION $C_8$ alkylaromatic hydrocarbons are generally considered to be valuable products, and para-xylene in particular is in high demand. On the other hand, $C_9$ and $C_{10}$ alkylaromatic hydrocarbons are not nearly as valuable but are typically produced as a byproduct in the same aromatic production processes used to produce $C_8$ alkylaromatic hydrocarbons. Various approaches have been used to convert the less valuable $C_9$ and $C_{10}$ alkylaromatic hydrocarbons into $C_8$ alkylaromatic hydrocarbons. One popular approach has been to transalkylate $C_9$ and $C_{10}$ alkylaromatic hydrocarbons along with benzene or toluene to form the $C_8$ alkylaromatic hydrocarbons. Specifically, trimethylbenzenes and tetramethylbenzenes have been transalkylated along with benzene and toluene to form xylenes. However, transalkylation reactions are equilibrium limited and the product contains a mixture of unreacted $C_9$ and $C_{10}$ alkylaromatic hydrocarbons along with the desired $C_8$ alkylaromatic hydrocarbons. To increase conversion, commercial processes have utilized a two-stage design with the first stage being a fixed bed reactor and the second stage being a separation unit. Unreacted $C_9$ and $C_{10}$ alkylaromatic hydrocarbons present in the reactor product stream are separated and recycled to the reactor; see for example U.S. Pat. No. 3,211,798 B1.

Once the $C_8$ alkylaromatic hydrocarbons have been produced, they may need to be separated from the unreacted $C_9$ and $C_{10}$ alkylaromatic hydrocarbons. The present invention provides a process for separating the desired $C_8$ alkylaromatic hydrocarbons from the less desired $C_9$ and $C_{10}$ alkylaromatic hydrocarbons using zeolite Y, or ion exchanged zeolite Y as an adsorbent. Zeolite Y has been used as an adsorbent in other applications such as the separation of the specific $C_8$ alkylaromatic hydrocarbon isomers. For example, U.S. Pat. No. 4,255,607 B1 discloses the separation of aromatic $C_8$ isomers by adsorption, preferably contacting the mixture with zeolite Y and then developing the resulting adsorption band with an ether having selectivity for para-xylene. Japanese Patent No. 79,037,129-B discloses contacting a mixture of $C_8$ aromatic hydrocarbons with a Y-type zeolite containing sodium, calcium, cobalt and or strontium as cation to selectively adsorb meta-xylene. U.S. Pat. No. 4,079,094 B1 discloses separating ethylbenzene from a mixture of xylene isomers by passing through a column of an adsorbent comprising type X or Y zeolite completely exchanged with strontium and potassium. The xylenes are selectively adsorbed and an ethylbenzene stream is withdrawn. U.S. Pat. No. 4,028,428 B1 discloses separating ethylbenzene from a mixture of xylene isomers by contacting the mixture with an adsorbent of a strontium-exchanged type X or type Y zeolite. The xylenes are selectively adsorbed and ethylbenzene may be withdrawn. U.S. Pat. No. 3,998,901 B1 discloses separating ethylbenzene from a mixture of xylene isomers under adsorption conditions with a type X or Y zeolite completely exchanged with strontium and potassium. U.S. Pat. No. 3,997,620 B1 discloses para-xylene being separated from mixtures containing other $C_8$ aromatics by contacting the mixture under adsorption conditions with type X or Y zeolite containing barium and strontium which selectively adsorbs the paraxylene.

The present invention solves a different problem from that of separating $C_8$ alkylaromatic hydrocarbon isomers. Instead, the present invention is directed to separating at least one $C_8$ alkylaromatic hydrocarbon from at least one $C_9$ or $C_{10}$ alkylaromatic hydrocarbon, which is a problem encountered in processes such as transalkylation. U.S. Pat. No. 4,956,552 B1 teaches that p-ethyltoluene may be separated from a mixture comprising p-ethyltoluene and at least one other component selected from $C_8$ alkylaromatic hydrocarbons and other $C_9$ aromatic hydrocarbons by contacting the mixture with zeolite Y ion exchanged with potassium. The p-ethyltoluene is selectively adsorbed and a raffinate stream containing the less strongly adsorbed alkylaromatic hydrocarbons is produced. The zeolite Y ion exchanged with potassium is contacted with a desorbent comprising 1,2,3,4-tetrahydronaphthalene or lower alkyl derivative thereof or an alkyl derivative of naphthalene at desorption conditions to effect the removal of p-ethyltoluene from the adsorbent as an extract stream. Applicants have discovered that in addition to zeolite Y ion exchanged with potassium, sodium zeolite Y as synthesized, without ion exchange, is effective to separate at least one $C_8$ alkylaromatic hydrocarbon from at least one $C_9$ or $C_{10}$ alkylaromatic hydrocarbon having at least one methyl or ethyl group, or a mixture thereof. Similarly, applicants have found that dealuminated sodium zeolite Y is successful in the claimed separation.

SUMMARY OF THE INVENTION

The purpose of the invention is to separate at least one $C_8$ alkylaromatic hydrocarbon from at least one $C_9$ or $C_{10}$ alkylaromatic hydrocarbon. The invention involves contacting a mixture containing (I) at least one $C_8$ alkylaromatic hydrocarbon and (II) at least one $C_9$ or $C_{10}$ alkylaromatic hydrocarbon having at least one methyl or ethyl group, or a mixture thereof, with dealuminated zeolite Y having a $SiO_2/Al_2O_3$ ratio in the range of from about 7 to about 25 and containing essentially sodium in the ion-exchangeable sites to selectively adsorb the $C_9$ or $C_{10}$ alkylaromatic hydrocarbon. The $C_9$ and/or $C_{10}$ alkylaromatic hydrocarbon(s) are more strongly adsorbed by the adsorbent relative to the $C_8$ alkylaromatic hydrocarbon. The $C_8$ alkylaromatic hydrocarbon may pass through the adsorbent or if weakly adsorbed, may be desorbed using a desorbent and is collected. The more strongly adsorbed $C_9$, $C_{10}$, or mixture of $C_9$ and $C_{10}$ alkylaromatic hydrocarbon(s) is desorbed using the desorbent and collected. In a more specific embodiment of the invention, the desorbent is selected from toluene, benzene, or a mixture thereof. In another more specific embodiment of the invention, the adsorbent is dealuminated zeolite Y having a $SiO_2/Al_2O_3$ ratio in the range of from about 7 to about 12.

DETAILED DESCRIPTION OF THE INVENTION

Figure 1:
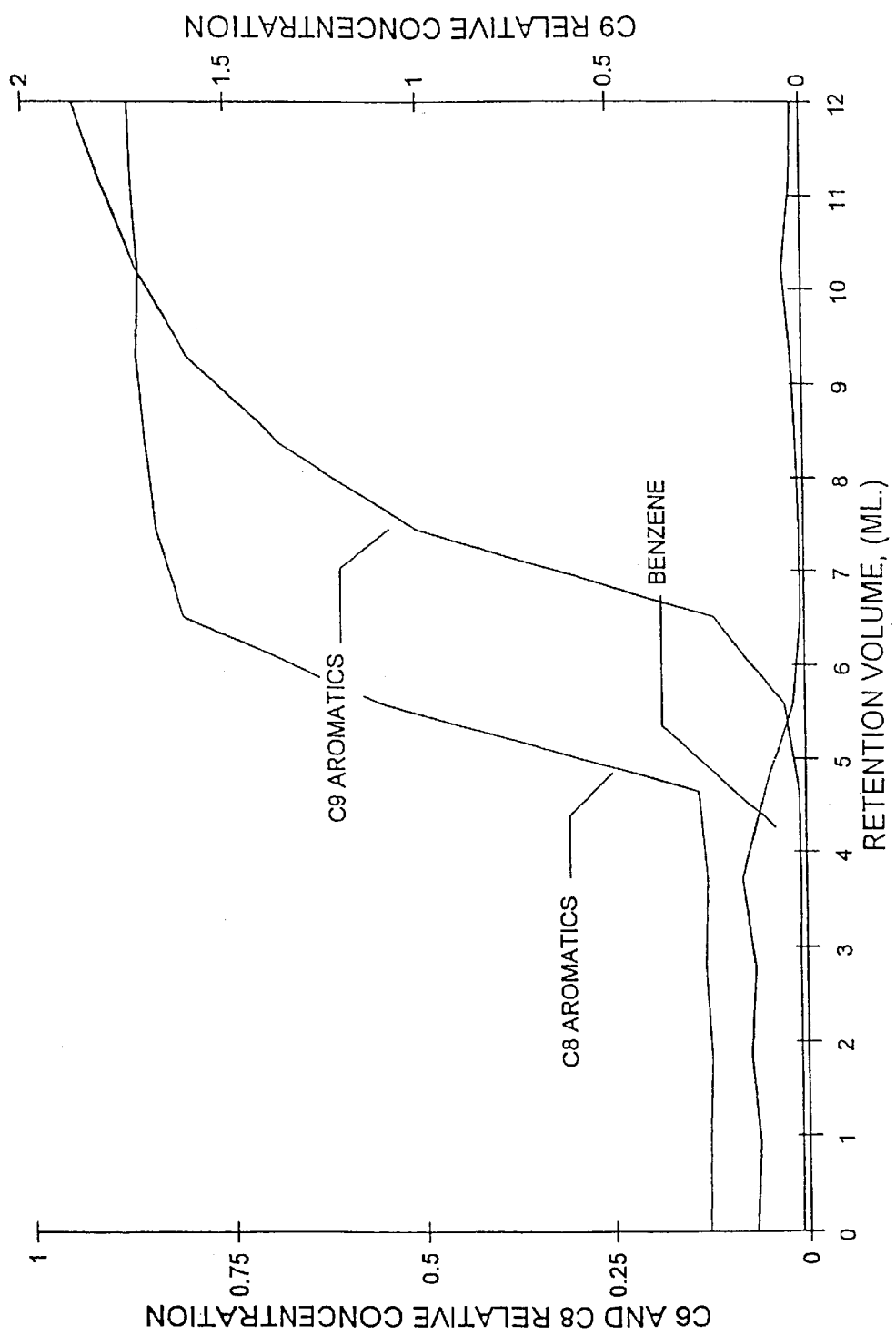
FIG. 1 is the chromatographic plot of the concurrent transalkylation of 1,2,4-trimethylbenzene and separation of the C$_8$ alkylaromatic hydrocarbon products using dealuminated Y zeolite as both the catalyst and adsorbent as described in Example 1. The C$_8$ alkylaromatic hydrocarbons are summed and the sum of the concentrations is plotted. Similarly, the C$_9$ alkylaromatic hydrocarbons are summed and the sum of the concentrations is plotted.

In general terms, the invention involves using an adsorbent in a separation process to separate at least one C$_8$ alkylaromatic hydrocarbon from at least one C$_9$ or C$_{10}$ alkylaromatic hydrocarbon. The mixture to be separated contains (I) at least one C$_8$ alkylaromatic hydrocarbon and (II) at least one C$_9$ or C$_{10}$ alkylaromatic hydrocarbon having at least one methyl or ethyl group, or a mixture thereof. The mixture is contacted with specific adsorbents chosen to have preferential selectivity for the C$_9$ or C$_{10}$ alkylaromatic hydrocarbons, described in detail below, to adsorb the C$_9$ or C$_{10}$ alkylaromatic hydrocarbons relative to the C$_8$ alkylaromatic hydrocarbons. The C$_8$ alkylaromatic hydrocarbons are carried with the fluid flow, removed from the system, and collected. A desorbent is used to desorb the C$_9$ or C$_{10}$ alkylaromatic hydrocarbons from the adsorbent which are then removed from the system and collected.

The specific adsorbents of the invention were discovered to have a selectivity for C$_9$ and C$_{10}$ alkylaromatic hydrocarbon reactants relative to that of C$_8$ alkylaromatic hydrocarbons. In other words, the adsorbent was discovered to be capable of preferentially adsorbing C$_9$ and C$_{10}$ alkylaromatic hydrocarbons relative to C$_8$ alkylaromatic hydrocarbons at the operating conditions of the present invention. Specifically, the adsorbent used in the present invention is sodium zeolite Y as synthesized and dealuminated zeolite Y having a SiO$_2$/Al$_2$O$_3$ ratio in the range of from about 5 to about 25, and preferably from about 7 to about 25 and from about 8 to about 25, and most preferably from about 7 to about 12. The sodium zeolite Y may be ion exchanged with calcium, strontium, a Group IB element, a Group VII element, or mixtures thereof and used successfully in the present invention. The dealuminated zeolite Y is obtained by dealuminating zeolite Y that is in the H$^+$form, washing, and then ion-exchanging with a metal selected from the group consisting of calcium, sodium, strontium, a Group IB element, a Group VIII element and mixtures thereof. In one embodiment of the invention, zeolite Y that is in the H$^+$form is dealuminated by, at least, washing, and then ion-exchanging with sodium to form the dealuminated zeolite Y having a SiO$_2$/Al$_2$O$_3$ ratio in the range of from about 7 to about 25 and consisting essentially of sodium in the ion-exchangeable sites. This adsorbent is generally termed dealuminated zeolite Y in the sodium form, or dealuminated sodium zeolite Y. Note that the selective adsorption is accomplished by the zeolite, but the overall adsorbent may be a combination of the zeolite and a binder material. The zeolite plus binder composite may be calcined, although calcination is not required.

The structure of zeolite Y is described, and further references are provided, in Meier, W. M.; Olson, D. H.; Baerlocher, Ch. *Atlas of Zeolite Structure Types*, 4$^{th}$ Edition, Elsevier: Boston, 1996, pp. 62–63 and 104–105. See also U.S. Pat. No. 4,940,830 B1, hereby incorporated by reference and U.S. Pat. No. 3,130,007 B1 which is hereby incorporated by reference in its entirety. By far, the most common process for making zeolite Y involves reagents containing sodium, such as sodium aluminate, sodium hydroxide, and sodium silicate, see U.S. Pat. No. 3,130,007 B1 and Ullmann's Encyclopedia of Industrial Chemistry volume A28 p. 485–487. Therefore, the commercially available product zeolite Y as synthesized, i.e., without further treatment, contains substantially sodium at the ion-exchangeable sites and has been referred to as "sodium zeolite Y" or simply "zeolite Y", see U.S. Pat. No. 3,130,007 B1 and Kirk-Othmer Encyclopedia of *Chemical Technology*, 4$^{th}$ Ed. Vol. 2 p. 253 which provides the molecular formula of "zeolite Y" as Na$_{55}$[(Al$_2$)$_{56}$(SiO$_2$)$_{136}$]·250H$_2$O. When one of ordinary skill in the art refers to "sodium zeolite Y" or "zeolite Y in the sodium form" it is understood to mean that no other metals are at the ion-exchangeable sites in an amount effective to alter the adsorptive properties of the zeolite. Hence, the zeolite Y as generally synthesized contains "substantially" sodium at the ion-exchangeable sites. The term "substantially" is used because some sites may be only partially exchanged or a cation from an impurity in a starting material may be present. However, if other cations were present as impurities in the reagents, it would not be expected that such cations would be present in the final product in an amount effective to change the adsorptive properties of the zeolite Y for the separation claimed herein. Theoretically, such impurities in the reagents may potentially cause a small amount of another zeolite to be formed. The composition and structure of zeolite Y is further discussed in Breck, D. W. Zeolite Molecular Sieves: *Structure, Chemistry, and Use*; John Wiley & Sons: New York, 1974; pp. 93, 97, and 177. Zeolite Y may be bound with a binding material. Calcination of bound sodium zeolite Y in air would result in the removal of all or a portion of the water associated with the sodium zeolite Y. Depending upon the temperature and water content, dealumination may also take place.

Dealumination is generally accomplished through steaming followed by acid washing. The steaming and acid washing results in the removal of alumina thereby changing the silica to alumina ratio from that of the as synthesized or as calcined sodium zeolite Y. Again, if cations were present as impurities in the reagents used for dealumination, it would not be expected that such cations would be present in the final product in an amount effective to change the adsorptive properties of the zeolite Y for the separation claimed herein. It is likely that such cations would be removed in the washing step. A preferred adsorbent is sodium zeolite Y as synthesized and a most preferred adsorbent is zeolite Y-54, a sodium zeolite Y at least partially ion exchanged with strontium; see Example 3. These preferred adsorbents may also be bound with a binding material and calcined. Two or more adsorbents may be used together.

Particular adsorbents may retain the individual isomers of $C_8$ alkylaromatic hydrocarbons differently, which may be advantageous in specific applications. For example, clay-bound sodium zeolite Y as calcined has a greater selectivity for meta-xylene as compared to para-xylene and ortho-xylene; see Example 2. Therefore, a product stream may be withdrawn that is depleted in meta-xylene as compared to an equilibrium mixture of all $C_8$ alkylaromatic hydrocarbon isomers.

The adsorbent is preferably used in a fixed bed mode at operating conditions of a temperature ranging from about 75° C. to about 300° C. and pressures from atmospheric to about 600 psig. The operating conditions should be chosen so that all components are in the same phase, gas or liquid. The gas phase allows higher mass transfer while the liquid phase provides higher adsorbent loading.

The desorbent must be capable of desorbing the $C_9$ and $C_{10}$ alkylaromatic hydrocarbon reactants. Examples of acceptable desorbents include benzene and toluene and a mixture thereof. The mixture to be separated contains at least one $C_9$ or $C_{10}$ alkylaromatic hydrocarbon preferably containing at least one methyl or ethyl group. Preferred $C_9$ and $C_{10}$ alkylaromatic hydrocarbons are trimethylbenzenes and tetramethylbenzenes and examples of specific suitable alkylaromatic hydrocarbons include, but are not limited to, toluene, 1,3,5-trimethylbenzene, 1,2,4-trimethylbenzene, 1,2,3-trimethylbenzene, and the tetramethylbenzene isomers. Other alkylaromatic hydrocarbons such as methylethylbenzenes and propylbenzenes may also be present in the mixture. The mixture to be separated should not contain components that would significantly alter the capacities or selectivities of the adsorbent or desorbent. The product stream withdrawn from the simulated moving bed will contain desorbent and the desired $C_8$ alkylaromatic hydrocarbon products which are usually ortho-meta- and para-xylenes. The product stream may be purified using techniques such as distillation or crystallization.

The examples are directed to systems containing both the adsorbents described herein and a transalkylation catalyst. The $C_8$ alkylaromatic hydrocarbons are produced within the system from transalkylation of the $C_9$ or $C_{10}$ alkylaromatic hydrocarbons with benzene or toluene or a mixture thereof. Then, the $C_8$ alkylaromatic hydrocarbons are separated from the $C_9$ or $C_{10}$ alkylaromatic hydrocarbons through contact with the adsorbent that selectively adsorbs the $C_9$ or $C_{10}$ alkylaromatic hydrocarbons. The $C_8$ alkylaromatic hydrocarbons are collected. A desorbent is used to desorb the $C_9$ or $C_{10}$ alkylaromatic hydrocarbons which are then collected.

Example 1

A 70 mL column was loaded with 34.9 grams of a single 20–40 mesh compound which is capable of functioning both as a catalyst and as an adsorbent, dealuminated sodium zeolite Y having a $SiO_2/Al_2O_3$ ratio of 6. The column was placed in a heated enclosure at 250° C. and maintained at process pressure of 28 psig using back pressure regulators. Toluene desorbent and hydrogen were directed into the columns at measured rates. A 20 mL pulse of 1,2,4-trimethylbenzene feed was introduced and the desorbent flow was resumed. The effluent of the system was condensed and analyzed by gas chromatography to obtain the composition of the effluent. FIG. 1 shows the concentration profiles of the effluent beginning with the background level of toluene desorbent and $C_8$ alkylaromatic hydrocarbons, the background level of $C_8$ alkylaromatic hydrocarbons is due to toluene disproportionation. The concentrations of each individual species in a carbon number class were summed and the sum of the concentrations plotted. A region of effluent enriched in $C_8$ alkylaromatic hydrocarbons elutes prior to a region enriched in $C_9$ alkylaromatic hydrocarbons showing that the separation of $C_8$ alkylaromatic hydrocarbons from the $C_9$ alkylaromatic hydrocarbons is occurring.

Example 2

Figure 2:
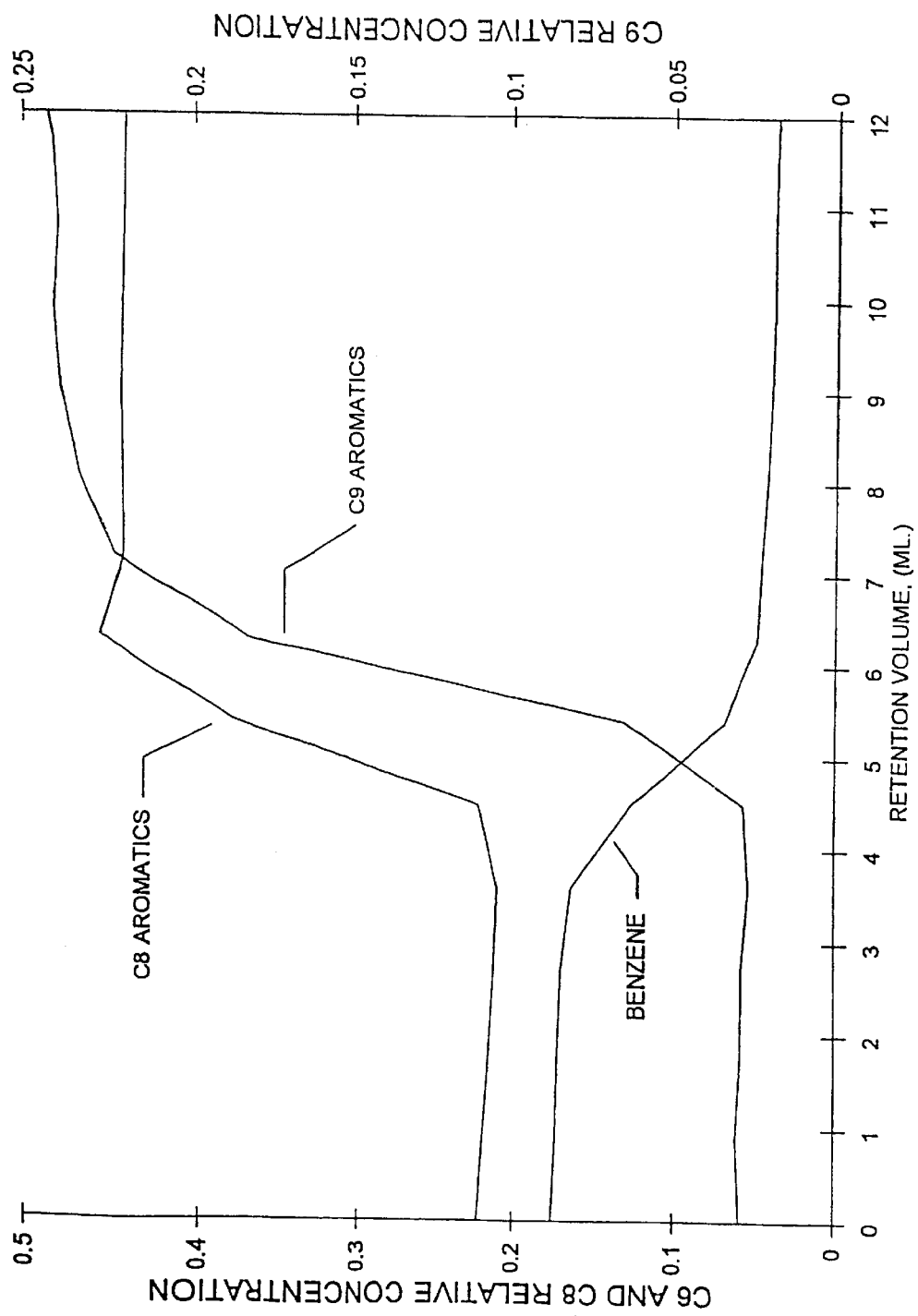
FIG. 2 is the chromatographic plot of the concurrent transalkylation of 1,3,5-trimethylbenzene and separation of the C$_8$ alkylaromatic hydrocarbon products using a homogeneous mixture of H-mordenite bound with alumina catalyst and Na—Y zeolite bound with clay adsorbent as described in Example 2. The C$_8$ alkylaromatic hydrocarbons are summed and the sum of the concentrations is plotted. Similarly, the C$_9$ alkylaromatic hydrocarbons are summed and the sum of the concentrations is plotted.

A 70 mL column was loaded with a homogeneous mixture of 20–40 mesh catalyst and adsorbent. The catalyst was H-mordenite bound with alumina (12.75 grams) and the adsorbent was clay-bound Na—Y zeolite as calcined (24.75 grams). The column was placed in a heated enclosure at 250° C. and maintained at process pressure of 62 psig using back pressure regulators. Toluene desorbent and hydrogen were directed into the columns at measured rates. A 20 mL pulse of a feed containing 50 mass percent toluene and 50 mass percent 1,3,5-trimethylbenzene was introduced and the desorbent flow was resumed. The effluent of the system was condensed and analyzed by gas chromatography to obtain the composition of the effluent. FIG. 2 shows the concentration profiles of the effluent beginning with the background level of toluene desorbent and $C_8$ alkylaromatic hydrocarbons; the background level of $C_8$ alkylaromatic hydrocarbons is due to toluene disproportionation. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that separation is occurring.

Example 3

57 Grams of clay bound Na—Y-54 adsorbent as calcined containing 10.42 weight percent aluminum (volatile free) and 6.92 weight percent sodium (volatile free) were loaded into a column. 92 Grams of $SrCl_2 \cdot H_2O$ were dissolved in 3 liters of water and the resultant solution was circulated through the column for 20 hours at 70° C. and ambient pressure. The solution was drained from the column and the adsorbent rinsed with 5 L of water. The adsorbent was unloaded from the column and dried in a drying oven for about 16 hours in air at 90° C. The dried adsorbent was analyzed using an inductively coupled argon plasma atomic emission spectrophotometer to have 9.03 weight percent aluminum, 1.77 weight percent sodium, and 4.36 weight percent strontium, all on a volatile-free basis. The adsorbent was then dried at 500° C. and loaded into a column.

Figure 3:
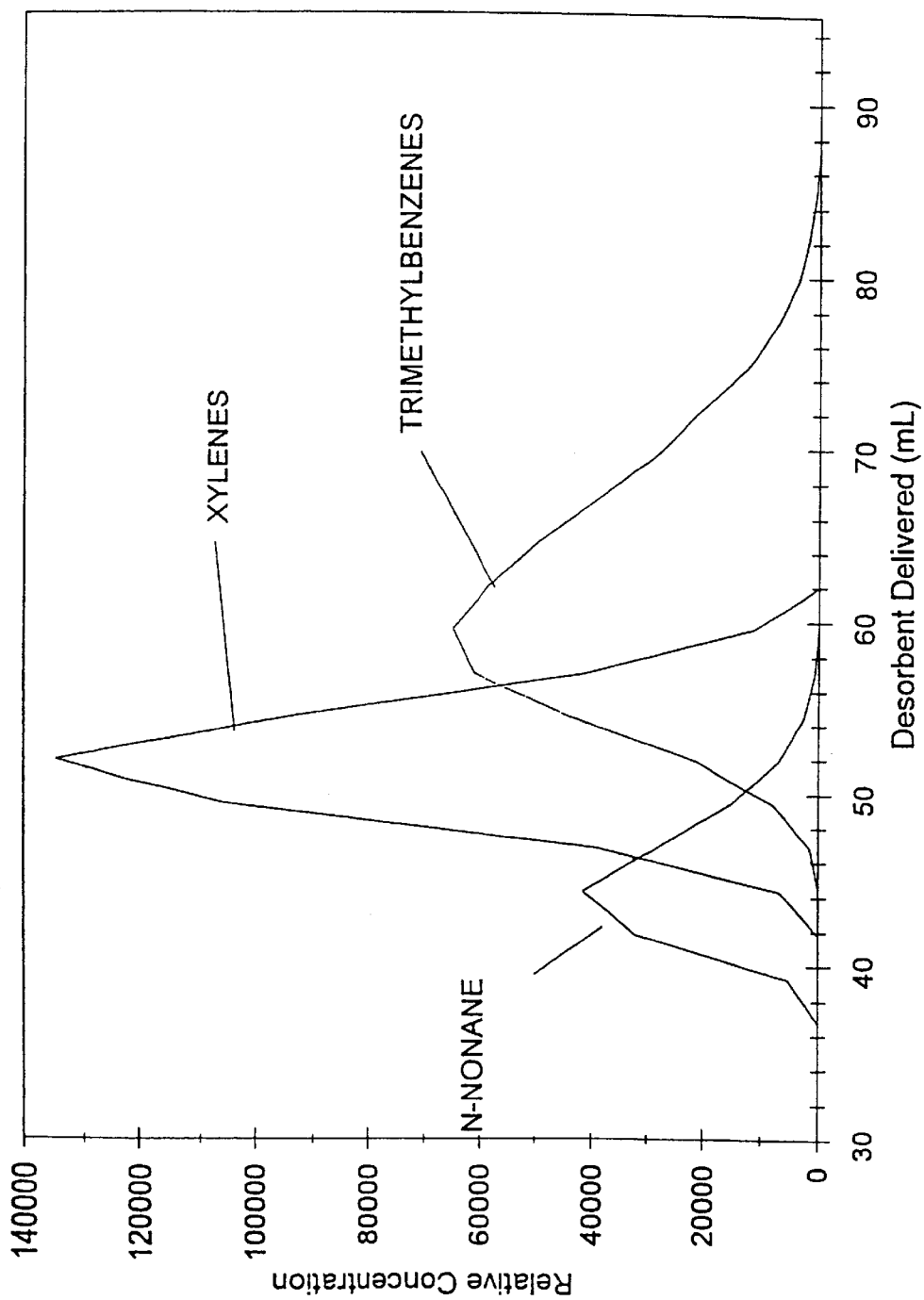
FIG. 3 is the chromatographic plot of the liquid phase separation of the C$_8$ alkylaromatic hydrocarbons from C$_9$ alkylaromatic hydrocarbons using a Na—Y zeolite ion exchanged with strontium adsorbent as described in Example 3. The C$_8$ alkylaromatic hydrocarbons are summed and the sum of the concentrations is plotted. Similarly, the C$_9$ alkylaromatic hydrocarbons are summed and the sum of the concentrations is plotted.

The column containing the dried adsorbent was placed in a heated enclosure at 150° C. and maintained at a pressure of 70 psig using back pressure regulators. Liquid phase toluene desorbent was directed into the columns at measured rates. A liquid phase 2 mL pulse of a feed containing equal parts normal nonane, ethylbenzene, para-xylene, meta-xylene, ortho-xylene, para-methylethylbenzene, meta-methylethylbenzene, ortho-methylethylbenzene, 1,2,3-trimethylbenzene, 1,2,4-trimethylbenzene and 1,3,5-trimethylbenzene was introduced and the desorbent flow was resumed. While in the column, the $C_8$ alkylaromatic hydrocarbons and $C_9$ alkylaromatic hydrocarbons were maintained in the liquid phase. The effluent of the system was analyzed by gas chromatography to obtain the composition of the effluent. FIG. 3 shows the concentration profiles of the effluent beginning with the background level of toluene desorbent. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that separation of the $C_8$ alkylaromatic hydrocarbons from the $C_9$ alkylaromatic hydrocarbons is occurring.

Figure 4:
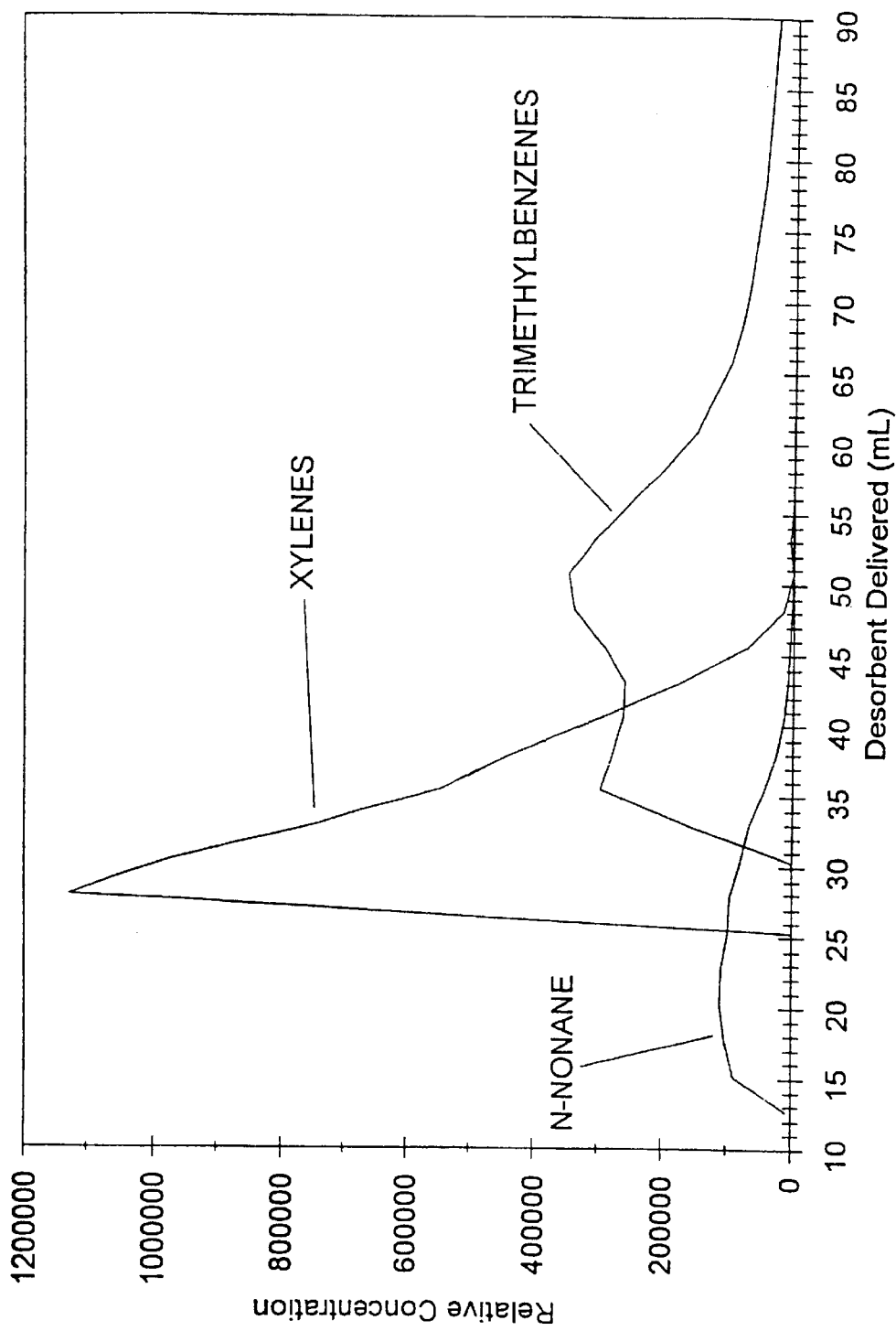
FIG. 4 is the chromatographic plot of the vapor phase separation of the C$_8$ alkylaromatic hydrocarbons from C$_9$ alkylaromatic hydrocarbons using a Na—Y zeolite ion exchanged with strontium adsorbent as described in Example 3. The C$_8$ alkylaromatic hydrocarbons are summed and the sum of the concentrations is plotted. Similarly, the C$_9$ alkylaromatic hydrocarbons are summed and the sum of the concentrations is plotted.

The pulse test was repeated with the components being maintained in the vapor phase. The column containing the dried adsorbent was again placed in a heated enclosure at 150° C. and maintained at a pressure of 10 psig using back pressure regulators. Toluene desorbent was directed into the columns at measured rates. A 20 mL pulse of a feed containing 32 mass percent toluene, 9.7 mass percent para-xylene, 14.8 mass percent meta-xylene, 9.4 mass percent ortho-xylene, 9.7 mass percent 1,3,5-trimethylbenzene, 20.0 mass percent 1,2,4-trimethylbenzene, and 4 mass percent 1,2,5-trimethylbenzene was introduced and the desorbent flow was resumed. While in the column, the $C_8$ alkylaromatic hydrocarbons and $C_9$ alkylaromatic hydrocarbons were maintained in the vapor phase. The effluent of the system was condensed and analyzed by gas chromatography to obtain the composition of the effluent. FIG. 4 shows the concentration profiles of the effluent beginning with the background level of toluene desorbent and $C_8$ alkylaromatic hydrocarbons; the background level of $C_8$ alkylaromatic hydrocarbons is due to toluene disproportionation. The concentrations of each individual species in a class were summed and the sum of the concentrations plotted. A region of effluent enriched in $C_8$ alkylaromatic hydrocarbons elutes region enriched in $C_9$ alkylaromatic hydrocarbons demonstrating that on of the $C_8$ alkylaromatic hydrocarbons from the $C_9$ alkylaromatic hydrocarbons is occurring.

What is claimed is:

1. A process of separating at least one $C_8$ alkylaromatic hydrocarbon from at least one $C_9$ or $C_{10}$ alkylaromatic hydrocarbon having at least one methyl or ethyl group, or a mixture thereof comprising:
    a) contacting a mixture containing (I) at least one $C_8$ alkylaromatic hydrocarbon and (II) at least one $C_9$ or $C_{10}$ alkylaromatic hydrocarbon having at least one methyl or ethyl group, or a mixture thereof, with dealuminated sodium zeolite Y having a $SiO_2/Al_2O_3$ ratio in the range of from about 7 to about 25 and consisting essentially of sodium in the ion-exchangeable sites, to selectively adsorb the $C_9$ or $C_{10}$ alkylaromatic hydrocarbon(s);
    b) collecting the $C_8$ alkylaromatic hydrocarbon; and
    c) desorbing the adsorbed $C_9$, $C_{10}$, or mixture of $C_9$ and $C_{10}$ alkylaromatic hydrocarbon(s) using a desorbent and collecting the $C_9$, $C_{10}$, or mixture of $C_9$ and $C_{10}$ alkylaromatic hydrocarbon(s).

2. The process of claim 1 wherein the desorbent is selected from the group consisting of toluene, benzene, and a mixture thereof.

3. The process of claim 1 wherein the dealuminated sodium zeolite Y has a $SiO_2/Al_2O_3$ ratio in the range of from about 7 to about 12.

4. The process of claim 1 further characterized in that the dealuminated sodium zeolite Y is bound with a binding material.

5. The process of claim 4 further characterized in that the bound dealuminated sodium zeolite Y is calcined.

* * * * *